US009227891B2

(12) United States Patent
Leflaive et al.

(10) Patent No.: US 9,227,891 B2
(45) Date of Patent: Jan. 5, 2016

(54) PROCESS FOR SEPARATION OF C8 AROMATIC COMPOUNDS WITH LIMITED RECYCLING

(75) Inventors: Philibert Leflaive, Mions (FR); Arnaud Baudot, Vernaison (FR); Helene Rodeschini, Lyons (FR); Tom Frising, Lyons (FR)

(73) Assignee: IFP BNERGIES NOUVELLES, Rueil-Malmaison (FR)

( * ) Notice: Subject to any disclaimer, the term of this patent is extended or adjusted under 35 U.S.C. 154(b) by 967 days.

(21) Appl. No.: 12/253,382

(22) Filed: Oct. 17, 2008

(65) Prior Publication Data

US 2009/0149686 A1    Jun. 11, 2009

(30) Foreign Application Priority Data

Oct. 18, 2007    (FR) ...................................... 07 07290

(51) Int. Cl.
| C07C 5/22 | (2006.01) |
| C07C 7/13 | (2006.01) |
| C07C 7/00 | (2006.01) |
| C07C 7/144 | (2006.01) |

(52) U.S. Cl.
CPC . C07C 7/13 (2013.01); C07C 7/005 (2013.01); C07C 7/144 (2013.01)

(58) Field of Classification Search
USPC ......... 585/828, 805, 478, 800, 804, 477, 480, 585/481, 482
See application file for complete search history.

(56) References Cited

U.S. PATENT DOCUMENTS

| 5,110,478 | A | * | 5/1992 | Haag et al. ..................... 208/118 |
| 6,369,287 | B1 | * | 4/2002 | Magne-Drisch et al. ..... 585/805 |
| 6,376,733 | B1 | * | 4/2002 | Ferraro et al. ................ 585/805 |
| 2002/0082462 | A1 | | 6/2002 | Ferraro et al. |
| 2005/0038308 | A1 | * | 2/2005 | Wolff et al. ................... 585/805 |
| 2005/0167338 | A1 | * | 8/2005 | Miller et al. ............. 208/310 R |

FOREIGN PATENT DOCUMENTS

| FR | 2 795 069 A1 | 12/2000 |
| FR | 2 844 790 A1 | 3/2004 |
| WO | WO 97/27161 A1 | 7/1997 |

OTHER PUBLICATIONS

L. van Dyk et al., "Xylene Isomerization in an Extractor Type Catalytic Membrane Reactor", Catalysis Today, vol. 104 (2005) pp. 274-280.

* cited by examiner

Primary Examiner — In Suk Bullock
Assistant Examiner — Sharon Pregler
(74) Attorney, Agent, or Firm — Millen, White, Zelano, Branigan, P.C.

(57) ABSTRACT

Process for the production of paraxylene from a C8 aromatic feedstock that comprises the following stages:
  A stage for separation by adsorption in a simulated moving bed SMB that produces an extract that contains at least 95% paraxylene and at least one raffinate R that contains ethylbenzene,
  A recycling of raffinate to the SMB separation stage after isomerization, in which R is separated in membrane separation means to obtain a first fraction F1 that is relatively high in ethylbenzene, which is purged, and an additional fraction F2 that is relatively low in ethylbenzene, which is recycled to the SMB after a single isomerization, preferably in the liquid phase.

16 Claims, 3 Drawing Sheets

:
PROCESS FOR SEPARATION OF C8 AROMATIC COMPOUNDS WITH LIMITED RECYCLING

FIELD OF THE INVENTION

The invention relates to the field of separations of paraxylene with a high level of purity from a stream that contains primarily aromatic compounds with eight carbon atoms. These C8 aromatic fractions are difficult to separate by distillation. Then, a family of processes and associated devices, known under the name of processes or devices of "chromatographic" separation or "simulated moving-bed" (according to English terminology) separation or "simulated counter-current" separation or "simulated co-current" separation, which we will refer to below by the name "SMB," are used.

The products other than the paraxylene are typically recycled to the SMB after isomerization.

The invention relates to a process for production of paraxylene with a high-purity level that is simpler to use than that of the prior art, in particular at the level of isomerization, and that has a small-capacity recycling loop.

EXAMINATION OF THE PRIOR ART

The SMB chromatographic separation is well known in the prior art. As a general rule, a simulated moving bed comprises at least three chromatographic zones, advantageously four or five, whereby each of these zones consists of at least one bed or column part and is encompassed between two successive supply or draw-off points. Typically, at least one feedstock F to be fractionated and one desorbent D (sometimes called eluent) are supplied, and at least one raffinate R and one extract E are drawn off. The supply and draw-off points are modified over time, typically shifted toward the bottom of a bed in a synchronous manner.

The SMB devices typically comprise at least one column (and often two, operating in series in a closed loop) of adsorbent beds Ai arranged in this column, separated by plates Pi with chamber(s) Ci for distributing and/or extracting fluids in or from various adsorbent beds, and controlled means for sequential distribution and extraction of fluids.

In an in-depth way, the prior art describes various devices and processes that make it possible to carry out the separation of feedstocks in a simulated moving bed. It is possible to cite in particular the U.S. Pat. No. 2,985,589, U.S. Pat. No. 3,214,247, U.S. Pat. No. 3,268,605, U.S. Pat. No. 3,592,612, U.S. Pat. No. 4,614,204, U.S. Pat. No. 4,378,292, U.S. Pat. No. 5,200,075, U.S. Pat. No. 5,316,821. These patents also describe in detail the operation of an SMB.

Several advantageous variants make it possible to improve the operation of this unit type by employing asynchronous change-overs. In a simplified way, these asynchronous change-overs are used to compensate for the dead volume(s) of the recirculation pump(s), as indicated in the U.S. Pat. No. 5,578,215, to work with a constant recycling flow rate on the recirculation pump so as to eliminate the surges in flow and pressure, as indicated in the U.S. Pat. No. 5,762,806, or finally to operate with at least two chromatographic zones, each of which is equivalent to a non-integer of adsorbent beds. This latter variant, as indicated in the U.S. Pat. No. 6,136,198, U.S. Pat. No. 6,375,839, U.S. Pat. No. 6,712,973 and U.S. Pat. No. 6,413,419, is known under the name of Varicol. Of course, these three variants can be combined. By extension, the above-mentioned Varicol-type separation processes or devices are assimilated according to the invention with simulated moving bed SMB separation processes or devices.

The production of high-purity paraxylene by separation by adsorption is well known from the prior art. The general state of the art that describes the production of very high-purity paraxylene is illustrated in, for example, the patent EP 1 081 121 A2.

The products other than paraxylene, designated PX (generally an orthoxylene mixture designated OX, metaxylene designated MX, and ethylbenzene designated EB, with traces of residual PX) are typically recycled to the SMB after isomerization. The use of a single isomerization, before recycling, however, poses problems: actually, the isomerization of the compounds MX and OX requires only mild isomerization conditions, whereas the ethylbenzene EB requires much more stringent conditions, leading to a certain dealkylation of MX/OX.

The patents FR 2792632 and FR 286238 of the applicant teach that it is possible to use two separate isomerization units within the loop that treats the aromatic compounds with 8 carbon atoms.

The diagram that is described in the patent FR 2792632 uses a distillation column, a so-called column for separation of ethylbenzene, which can have up to 200 plates and is to be operated at a very high reflux rate. At the top of this distillation column, a first stream is drawn off, and said stream is a very ethylbenzene-rich fraction that is isomerized in the gaseous phase under the following relatively stringent conditions: temperature of higher than 300° C., preferably 360° C. to 480° C., pressure of lower than 2.5 MPa and preferably 0.5 to 0.8 MPa, volumetric flow rate of less than 10 $h^{-1}$, preferably between 0.5 and 6 $h^{-1}$, hydrogen to hydrocarbon molar ratio of less than 10, and preferably between 3 and 6. The catalyst is typically a bifunctional catalyst (acid function produced by an acid zeolite and metal function produced by the use of a noble metal). It typically comprises an EUO-type-structural-type zeolite, for example in particular the EU1 zeolite, the ZSM-50 zeolite or the TPZ-3 zeolite, and preferably contains at least one metal of group VIII of the periodic table that is preferably selected from among palladium and platinum, as described in, for example, the patents or patent applications EP42226A1, U.S. Pat. No. 4,640,829, EP51318A1 and FR2772752A1.

The liquid-phase isomerization of the column bottom, rich in MX and OX, can be produced under the following relatively mild conditions: temperature of less than 300° C. and preferably between 200 and 260° C., pressure of less than 4 MPa and preferably between 2 and 3 MPa, volumetric flow rate of less than 10 $h^{-1}$ and preferably between 2 and 4 $h^{-1}$, whereby the catalyst is, for example, based on ZSM-5 zeolite, as indicated in the U.S. Pat. No. 4,435,608, U.S. Pat. No. 5,981,817 (page 2) and U.S. Pat. No. 6,924,405. The advantage of the liquid-phase isomerization, besides the energy consumption aspect that is lower, is to make possible the use of an acid catalyst only, and it is therefore much less expensive in production because it does not comprise noble metal.

The patent FR 2862638 makes it possible to maintain the advantages that are linked to the use of two separate isomerizations by operating these isomerizations on two raffinates, which eliminates the drawback of one very major distillation column.

However, these two patents describe a two-isomerization unit, which is complex and expensive in terms of investments as well as in terms of operating costs.

The use of membrane separation modules (permeation through a membrane) in the aromatic loop is furthermore well known to one skilled in the art. The application of the membrane separation techniques has shown good perspectives because i) they are simple processes, ii) they have a low energy consumption, iii) they can be extrapolated easily, and iv) they do not require additional products.

The power of separation of a membrane material can be based on a size effect; this is then a matter of molecular sieving. It is also possible to use a membrane material that has a specific affinity for one of the molecules to be separated: the selective adsorption of this molecule in the pores of the membrane increases its power to drive diffusion and at least partially prevents the adsorption of the second radical. This is thermodynamic affinity.

The membrane separation processes require a driving force that can be a difference of chemical potential between upstream and downstream or else a pressure gradient. For example, from the permeate side, it is common to maintain low pressures by using vacuum pumps or low-temperature condensers.

On the side of the feedstock, the driving force is applied by the use of high partial pressures by means of pumps or compressors, or by high temperatures.

There are so-called porous membranes and so-called dense membranes, whereby the separation processes are based on the molecular sieving in the first case and on a solubilization-diffusion process in the second case. It is also possible to classify the membrane materials based on their organic or inorganic chemical nature.

In the documents of the prior art, the separation performance levels of the membranes are generally described by means of two parameters: permeability and selectivity.

The permeability is defined as the flow density of the material passing through the membrane, relative to the thickness of said membrane, and to the partial pressure difference of the compounds that pass through the membrane that is applied between the upstream and downstream faces.

The selectivity of the membrane for the component A relative to the component B is defined as the ratio of the permeabilities of the two components A to B. The permeability is measured in barrer (1 barrer=$10^{-10}$ $cm^3 \cdot cm/cm^2/cm_{Hg} \cdot s$).

In the case of the separation of a binary mixture, the separation factor can be calculated in two ways: either starting from permeabilities obtained in a pure element (this is then ideal selectivity or permselectivity) or starting from data from the streams in a mixture (this is then mixture selectivity or a separation factor).

The U.S. Pat. No. 6,376,733 has a process for producing paraxylene that involves an simulated moving bed SMB separation with a recycling loop that comprises a membrane module and two isomerizations. It uses zeolitic membranes that have a greater permeability for ethylbenzene (and paraxylene) than for the other xylenes. The installation that is described is as complex, however, as that of the patents FR 2792632 and FR 2862638.

The patent EP 1182182 also proposes a process for producing paraxylene that involves a membrane module. Unlike in U.S. Pat. No. 6,376,733, EP 1182182 proposes the use of the membrane process by itself to produce pure paraxylene and does not consider the entire aromatic loop or its optimization.

The patent applications US2005/0167338 A1 and US2005/0171395 A1 have processes that involve a membrane module followed by another process for the production of pure paraxylene and pure metaxylene without mentioning a modification of the isomerization conditions.

SUMMARY DESCRIPTION OF THE INVENTION

An object of this invention is to reduce significantly the size of the train of isomerizations and the capacity of the recycling loop that is typically used in the SMB separation units of the C8 aromatic fraction, as described in, for example, the patents or patent applications U.S. Pat. No. 6,376,733, FR 2792632 and FR 2862638.

Another object of the invention is to carry out this simplification and this reduction of capacity without requiring complex means or entraining heavy operating costs. In particular, the invention makes it possible either to use an isomerization in a gaseous phase of reduced size, under less stringent conditions leading to less dealkylation of MX/OX, or to avoid the implementation of a gas-phase isomerization by using only one liquid-phase isomerization. In this latter case, this makes it possible to use an acid catalyst instead of a bifunctional acid-noble metal catalyst, which is much more expensive in production.

Finally, it makes it possible to prevent the implementation that is sometimes carried out of an expensive distillation column of the raffinate to obtain the separation of ethylbenzene.

For this purpose, the invention proposes separating an ethylbenzene-rich effluent upstream from the recycling loop by means of a suitable membrane module to purge this ethylbenzene-rich effluent from the recycling loop so that it does not cause swelling of this recycling loop and to eliminate simultaneously the second isomerization that is generally in the gaseous phase, expensive in terms of investment and requiring a significant operating cost. The sole remaining isomerization treats a stream that is low in ethylbenzene and can therefore operate in the gaseous phase under less stringent conditions, or preferably in the liquid phase without causing a swelling of the recycling loop by accumulation of ethylbenzene that is not converted by isomerization.

The evacuated, thus purged, ethylbenzene-rich effluent can optionally be treated by one or more purification stages so as to produce ethylbenzene that can be used as feedstock in a styrene production unit or else fed to a gasoline pool (mixing zone for gasoline production).

The process of the invention thus makes it possible both to eliminate the specific isomerization unit of the ethylbenzene as well as to reduce the recycling flow rates in the aromatic loop with an equal production capacity or to increase the production capacity with an equal recycling flow rate. The ethylbenzene purge makes it possible to avoid the accumulation of this compound without using isomerization in the gaseous phase or by using only one isomerization in a less stringent and therefore more economical gaseous phase.

A preferred version of the invention relates to a process for producing paraxylene with a very high level of purity comprising an SMB separation that produces two different distilled raffinates, R and R*, only one of which R, high in ethylbenzene, is supplied with the membrane separation.

This makes it possible to reduce the size and/or the number of membrane modules that are necessary to this separation.

The invention is not linked to a particular process or catalyst of isomerization, or to a particular process for separation in a simulated moving bed or even to a particular separation membrane, but to a linking of stages making it possible to reduce the flow rate of the isomerization loop and in a general way its expense as much in terms of investment as in terms of operating cost.

DETAILED DESCRIPTION OF THE INVENTION

More generally, the invention relates to a process for producing paraxylene from an aromatic hydrocarbon feedstock containing xylenes and ethylbenzene, whereby the process successively comprises the following stages:

A stage for separation by adsorption in a simulated moving bed SMB that produces, on the one hand, a distilled extract E that comprises at least 95% paraxylene, and, on the other hand, at least one distilled raffinate R that contains ethylbenzene, and optionally another distilled raffinate R* with an ethylbenzene content of less than that of R, The recycling of at least a part of the distilled raffinate R or, if necessary, distilled raffinates R and R* upstream from the simulated moving bed SMB after isomerization(s), in which at least a part of R is separated in membrane separation means through a membrane that has a selectivity for ethylbenzene relative to the orthoxylene and to the metaxylene, to obtain a first fraction F1 that is relatively high in ethylbenzene, which is purged in at least its larger part, and at least one additional fraction F2 that is relatively low in ethylbenzene, which is recycled after a single isomerization stage.

Preferably, this single isomerization stage is carried out exclusively in the liquid phase. According to the invention, "liquid-phase isomerization" designates an isomerization in which at least the larger part of the isomerization feedstock remains in the liquid phase. If this is not the case, the isomerization will be considered as being "in the gaseous phase."

It is possible, however, to use a gaseous-phase isomerization, typically with relatively moderate stringency, for example with a volumetric flow rate VVH of between 6 $h^{-1}$ and 15 $h^{-1}$, in particular between 8 $h^{-1}$ and 12 $h^{-1}$, with the above-mentioned pressure and temperature conditions and the catalysts, whereas the typical VVH conditions that are generally used are between 0.5 $h^{-1}$ and 6 $h^{-1}$, as indicated above.

The invention makes it possible, using a selective purge of an ethylbenzene-rich stream, to avoid a swelling of the recycling loop of ethylbenzene, even after liquid-phase isomerization, whereby the ethylbenzene is relatively more refractory with isomerization. This is taken advantage of by limiting the severity of the isomerization unit in the gaseous phase, or preferably by eliminating this isomerization in the gaseous phase that is most often used in the prior art—a unit that is expensive in terms of investment and operating fees—in favor of a liquid-phase isomerization.

Typically, the entirety of said part of the distilled raffinate R, or, if necessary, of the distilled raffinates R and R*, which is not purged, is recycled upstream from the separation stage by adsorption in simulated moving bed SMB, after having been previously subjected to the sole isomerization stage and optionally to the separation and the evacuation of compounds that do not have 8 carbon atoms.

A single isomerization unit is used, including when there are two raffinates R and R*. In this case, the common isomerization typically treats the mixture of raffinate R* and the fraction F2 that is relatively low in ethylbenzene, obtained from the membrane separation, generally carried out on the single raffinate R.

The isomerization stage is preferably carried out in a phase that is for the most part and preferably essentially liquid. It is typically operated under the following conditions:

Temperature of less than 300° C., preferably between 200° C. and 260° C.,
Pressure of less than 4 MPa, preferably between 2 and 3 MPa,
Hourly volumetric flow rate of less than 10 $h^{-1}$, preferably between 2 and 4 $h^{-1}$.

All of the catalysts that are able to isomerize the hydrocarbons with 8 carbon atoms are suitable for the isomerization unit of this invention. Preferably, a catalyst that contains a ZSM-5-type zeolite as indicated in the U.S. Pat. No. 4,435,608, U.S. Pat. No. 5,981,817 (page 2) and U.S. Pat. No. 6,924,405 will be used.

Thus, unlike in the prior art, this invention involves only one isomerization stage, either in the gaseous phase at a typically relatively high VVH or preferably in the liquid phase, which leads to significant savings both in terms of the investments (in particular regarding the initial catalyst feedstock) and in terms of the operating costs. This does not bring about, however, a swelling of the recycling loop by accumulation of ethylbenzene owing to its relatively low isomerization because of the implementation of an ethylbenzene purge outside of the loop.

The purged ethylbenzene-rich fraction F1 can be used as a component in the gasoline pool. It may be advantageous, however, to use it as an ethylbenzene source for petrochemical purposes, in particular for the production of styrene. It is possible in particular to carry out a purification of the ethylbenzene-enriched fraction F1 that is purged to obtain ethylbenzene with a purity that is at least equal to 98%, and even 99% or more.

This purification of the enriched fraction F1 can be carried out by any means that are known to one skilled in the art. It is possible in particular to carry out a purification essentially by simple distillation or even azeotropic distillation, as described in the reference work: Procédés de pétrochimie: caractéristiques techniques et économiques [Petrochemistry Processes: Technical and Economic Characteristics]. Volume 1, Le gaz de synthèse et ses dérivés, les grands intermédiaires hydrocarbonés [The Synthesis Gas and its Derivatives, The Major Hydrocarbon Intermediate Compounds]/A. Chauvel, G. Lefebvre, J. P. Catry; Publications of the French Petroleum Institute, Editions Technip., 1977, pages 235-237. It is also possible to use the liquid-liquid extraction, with or without complexing in the presence of an ionic liquid or a non-ionic liquid such as HF—BF3, introduced in a super-stoichiometric quantity, for example. It is also possible to use a combination of several of these techniques.

In general, F1 and F2 are respectively the permeate and the retentate that are obtained by the membrane separation. This therefore means that the membrane is permselective for the ethylbenzene with regard to the orthoxylene and metaxylene.

The membrane separation means comprise one or more membrane module(s): The membrane module, a part of, or all of the membrane modules comprise(s) a membrane that is typically permselective to the ethylbenzene that can comprise at least one compound of polymeric nature, or else at least one compound of inorganic nature. The membranes that are used in the membrane module may or may not be composites, deposited on a substrate or not supported, asymmetrical or not. The shape and the nature of the membrane module is not critical in this invention, whereby the parameters guiding the selection of the module are based primarily on criteria of use, cost and effectiveness.

It is possible to use in particular a membrane that is permselective to ethylbenzene, with a molecular sieve base or a polymer base. This membrane offers a great permeability to the ethylbenzene, preferably more than 0.1 barrer.

The selectivity toward ethylbenzene relative to orthoxylene and metaxylene is preferably more than 25 and even more preferably more than 50.

The pressure difference between upstream and downstream from the membrane is preferably between 0.1 and 10 MPa and even more preferably between 0.1 and 5 MPa.

The temperature of the membrane module depends on the membrane that is used, and it is typically between the ambient temperature and 250° C., preferably between the ambient temperature and 175° C., and even more preferably between the ambient temperature and 120° C.

The recovery rate of ethylbenzene is more than 50% and preferably more than 70%.

This membrane can consist of, for example, and in a non-limiting way, the zeolite(s) ZSM-5, ZSM-11, ZSM-22, ZSM-23, ZSM-35, ZSM-48, ZSM-57, SUZ-4, SSZ-23, SSZ-25, SSZ-28, SSZ-32, SSZ-36, NU-87, silicalite or granules of at least one natural or synthetic silicalite that are dispersed in a polymeric material or else borosilicate granules and/or silico-aluminophosphate granules and/or aluminophosphate granules and/or granules of other zeolites that are dispersed in a polymeric material, or polymers such as polyimide, polysulfone, polyethersulfone, polyamide, polycarbonate, poly(amide imide) and polyester. The shaping of the membranes is not limiting; they can be used in sheets, in disks, in hollow fibers, in spiral modules, ou in any other suitable form. It is possible in particular to use the membrane that is described in the U.S. Pat. No. 5,824,617, or one of the membranes described in the articles: "Aromatic Permeation through Crystalline Molecular Sieve Membranes" (which "perméation d'aromatiques à travers des membranes en tamis moléculaire cristallin" means), J. L. Falconer, C. J. Gump, V. A. Tuan, R. ID. Noble, Ind. Eng. Chem. Res., 40, 2 565-577, 2001; and "permeation of Aromatic Hydrocarbon Vapors through Silicalite-Zeolite Membranes" (which "perméation d'hydrocarbures aromatiques en phase vapeur à travers des membranes zéolithe de type silicalite" means), C. D. Baertsch, H. H. Funke, J. L. Falconer, R. ID. Noble, J. Phys. Chem., 101, 7676-7679, 1996).

The paraxylene is produced at a purity of at least 95% by weight, typically with a very high purity of at least 99.5%, and even most often at least 99.7% by weight.

The SMB separation unit by adsorption in a simulated moving bed comprises at least a first adsorption column that operates in a simulated moving bed and contains a number of beds of an adsorbent, preferably interconnected in a closed loop and having a different selectivity for paraxylene, ethylbenzene, metaxylene, and orthoxylene, whereby this column comprises at least four zones of operation: a zone I for desorption of the paraxylene encompassed between the injection of a desorbent and the sampling of an extract, a zone II for desorption of ethylbenzene, orthoxylene and metaxylene encompassed between the sampling of the extract and the injection of the adsorption feedstock, a zone III for adsorption of paraxylene encompassed between the injection of the feedstock and the draw-off of a raffinate, and a zone IV between the draw-off of raffinate and the injection of desorbent. Typically, two columns in series are used interconnected in a closed loop.

The SMB separation unit is operated in general at a temperature of between 20° C. and 250° C., preferably between 90° C. and 210° C., and even more preferably between 160° C. and 200° C., and under a pressure of between the bubble pressure of xylenes at the operating temperature and 2 MPa. The desorbent that is used in the SMB unit is generally selected from among paradiethylbenzene, toluene, paradifluorobenzene or diethylbenzenes in a mixture. The volumetric ratio of the desorbent to the feedstock in the SMB unit is typically between 0.5 and 2.5 and preferably between 1.0 and 1.7.

According to a preferred characteristic variant of the invention, a separation into a simulated moving bed SMB that produces 2 distilled raffinates R and R*, including a first distilled raffinate R that contains ethylbenzene and another distilled raffinate R* with an ethylbenzene content of less than that of R, is used. Typically, the fraction F1 that is relatively high in ethylbenzene (generally the permeate) is purged, and, on the one hand, the fraction F2 that is relatively low in ethylbenzene (generally the retentate) as well as, on the other hand, the distilled raffinate R* upstream from the simulated moving bed SMB are recycled, after F2 and R* have been previously subjected to a liquid-phase-type isomerization.

The SMB separation unit then consists of one or more adsorption columns that comprise at least five operating zones delimited by the injection of the feedstock, the desorbent, and the draw-offs of an extract that contains paraxylene, an intermediate raffinate (or first raffinate) that contains ethylbenzene, and a second raffinate that contains primarily orthoxylene and metaxylene. Zone I for desorption of the paraxylene is encompassed between the injection of the desorbent and the sampling of the extract. Zone II for desorption of ethylbenzene, metaxylene and orthoxylene is encompassed between the sampling of the extract and the injection of the feedstock. Zone IIIA for adsorption of paraxylene is encompassed between the injection of the feedstock and the draw-off of the intermediate raffinate. Zone IIIB for adsorption of ethylbenzene is encompassed between the draw-off of the intermediate raffinate and the draw-off of the second raffinate, and zone IV is between the draw-off of the second raffinate and the injection of the desorbent.

Drawn off from this or these adsorption column(s) in a simulated moving bed is an extract that essentially consists of paraxylene and desorbent and that is sent into a distillation column from which there is drawn off, on the one hand, paraxylene with very high purity (preferably more than 99.7%), and, on the other hand, the desorbent that is virtually free of paraxylene that can be recycled at least in part at the input of the adsorption stage.

In contrast, an intermediate ethylbenzene-enriched raffinate is also drawn off that is sent into a distillation column from which there is drawn off, on the one hand, a (first) distilled raffinate R that is rich in ethylbenzene that is sent at least in part to the membrane module and from which there is drawn off, on the other hand, the desorbent that is virtually free of ethylbenzene that is recycled at least partly at the input of the simulated moving bed adsorption stage.

Finally, a second raffinate stream that essentially consists of metaxylene, orthoxylene and desorbent is drawn off and is sent into a distillation column from which there is drawn off, on the one hand, the second distilled raffinate R*, mixture of metaxylene and orthoxylene that is virtually free of desorbent, and from which there is drawn of, on the other hand, the desorbent that is virtually free of metaxylene and orthoxylene. This desorbent is recycled at least in part at the input of the adsorption stage. This mixture R* of metaxylene and orthoxylene is sent directly to the isomerization stage that works in the liquid phase or in the gaseous phase, and preferably in the liquid phase.

The first distilled raffinate (or intermediate raffinate) R, from which its desorbent is removed, is sent into the membrane module. A fraction F1 that is still enriched with ethylbenzene that is purged is drawn off from the membrane module and is optionally sent to an optional stage for purification of the ethylbenzene. In contrast, the fraction F2 that is relatively low in ethylbenzene (typically the retentate) is drawn off, and said fraction F2 consists essentially of metaxylene and orthoxylene that is sent to the isomerization unit, generally in the liquid phase, typically mixed with R*.

DESCRIPTION OF THE FIGURES

The invention will be better understood from reading the figures in which.

The reference numbers of the corresponding elements are identical for all of the figures.

Figure 1:
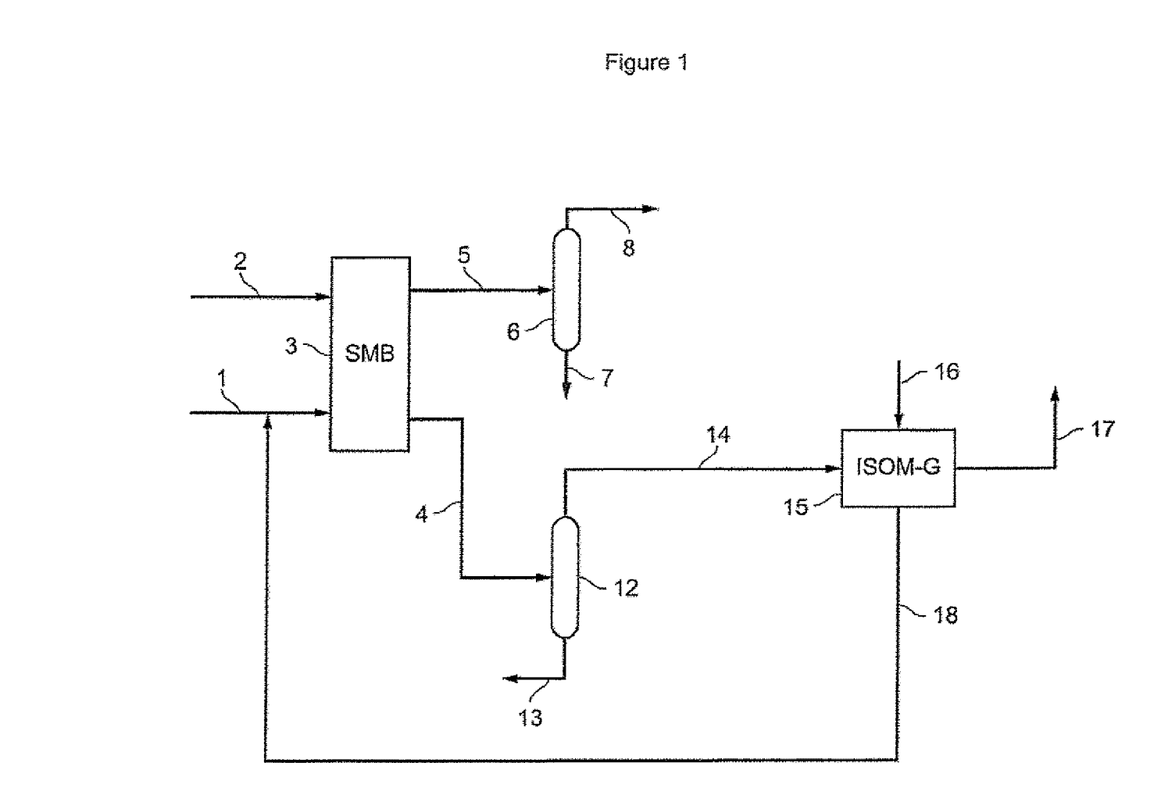
FIG. 1 diagrammatically shows an installation for separation of C8 aromatic compounds according to the prior art.

Reference is now made to FIG. 1, representative of the prior art.

A separation of a feedstock of C8 aromatic compounds, comprising the compounds PX, OX, MX and EB, is carried out.

The adsorption stage is carried out in a simulated moving bed adsorption column or chromatographic column 3 that receives as input the feedstock to be separated via line 1 as well as the desorption solvent or desorbent via line 2, for example paradiethylbenzene (PDEB). The column comprises at least four zones: zone I for desorption of the PX between the injection of the desorbent and the draw-off of the PX-rich extract, zone II for desorption of MX, OX and EB between the draw-off of PX and the injection of the feedstock, zone III for adsorption of PX between the injection of the feedstock and the draw-off of the raffinate that consists of MX, OX and EB, and zone IV between the draw-off of raffinate and the injection of desorbent. From this adsorption column or chromatographic column 3, a raffinate that is high in MX, OX, EB and desorbent and low in PX is therefore drawn off via line 4, and an extract that is high in PX and in desorbent and low in MX, OX and EB is drawn off via line 5.

The extract is distilled in a column 6 to obtain the recycled desorbent via line 7 and the distilled extract (E) via line 8, high-purity PX compound, for example at 99.8% by weight. FIG. 1 shows a direct separation with high purity ("stand alone," in English). A hybrid unit could also be used. In this case, the distilled extract E would be at a purity of about 95% by weight and would then be purified in a crystallization unit to obtain the PX with at least 99.7% of purity (typical commercial specification) and a mother liquor that is generally recycled to the SMB.

The raffinate is distilled in a column 12 to obtain the recycled desorbent via line 13 and the distilled raffinate (R) that is evacuated via line 14, low in PX and high in MX, OX and EB.

The distilled raffinate (R) is sent via line 14 into an isomerization unit 15 in the gaseous phase (ISOM-G) to make it possible to isomerize ethylbenzene adequately, as well as OX and MX, which inevitably undergo a certain dealkylation. This ISOM-G unit typically receives a hydrogen stream that is supplied via line 16. Before recycling to the SMB of the isomerizate via line 18, the compounds not including the C8 fraction (with 8 carbon atoms) that are contained in the isomerization effluents are evacuated via line 17.

Figure 2:
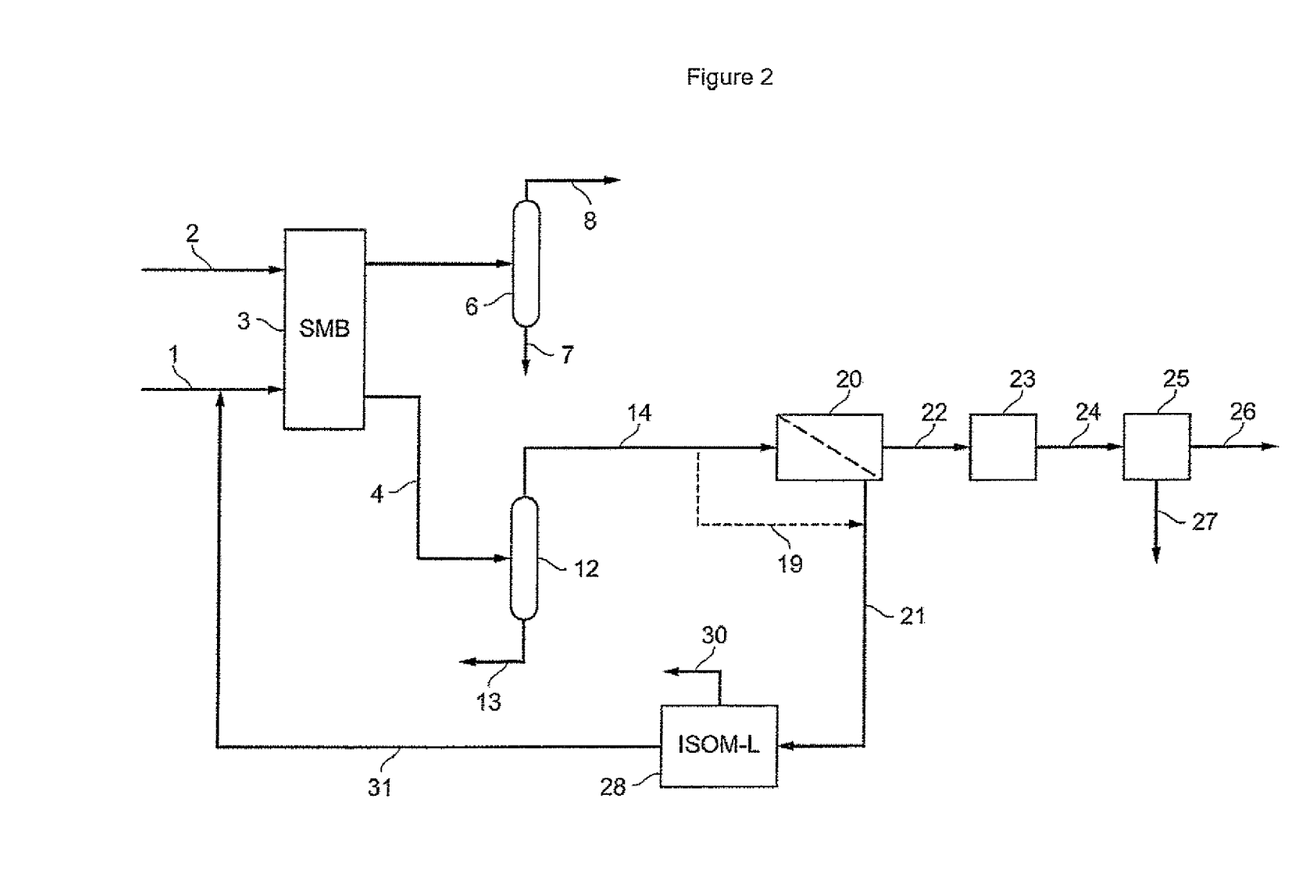
FIG. 2 diagrammatically shows an installation for separation of C8 aromatic compounds for the implementation of the process according to the invention, in which a single distilled raffinate R is used.

Reference is now made to FIG. 2, whose installation allows the implementation of the process according to the invention, and whose simulated moving bed SMB separation unit produces a single distilled raffinate R, as in Example 1.

The SMB separation and the purification of the extract are carried out in an identical manner to that of FIG. 1. The distilled raffinate R that circulates in line 14 and that is high in OX, MX and EB in contrast is not isomerized directly, but is sent into a membrane separation unit 20 that comprises one or more separation modules with a zeolitic membrane, polymer, or zeolite and polymer mixture that is permselective for the ethylbenzene EB. This unit produces a permeate 22 that is relatively high in EB, and low in OX and MX, which is evacuated via line 22 of the recycling loop to the SMB unit, and a retentate that is relatively high in OX and MX and low in EB that circulates in line 21.

It is possible in particular to use one of the membranes defined above.

A fraction of the distilled raffinate R optionally may bypass the membrane separation via line 19, thereby reducing its capacity.

The permeate that circulates in line 21 is isomerized in an isomerization unit 28, preferably in the liquid phase (ISOM-L), conventionally without the addition of hydrogen. After isomerization effluents are separated, a stream of fractions excluding C8 is evacuated via line 30. The isomerate is recycled via line 31 upstream from the SMB unit.

As a variant, the unit 28 can be an isomerization unit in the gaseous phase with a catalytic volume that is typically reduced relative to the catalytic volume of that of FIG. 1: actually, since ethylbenzene has been evacuated via line 22, even a limited isomerization of this ethylbenzene makes it possible to operate without excessive swelling of the recycling loop by the ethylbenzene that is not converted (not isomerized).

The ED-rich permeate that circulates in line 22 is dehydrogenated in a dehydrogenation unit 23 for the conversion of the ethylbenzene EB into styrene. The effluent of this unit that exits via line 24 is then separated in a separation unit 25 to produce styrene that exits via line 26 and a stream of residual compounds that circulate in line 27.

The dehydrogenation unit 23 can be produced, for example, as it is described in the patent FR 2844790, pages 8, 12, and 13.

The separation unit 25 can be produced, for example, as it is described in the patent FR 2844790, pages 9, 13 and 14.

Figure 3:
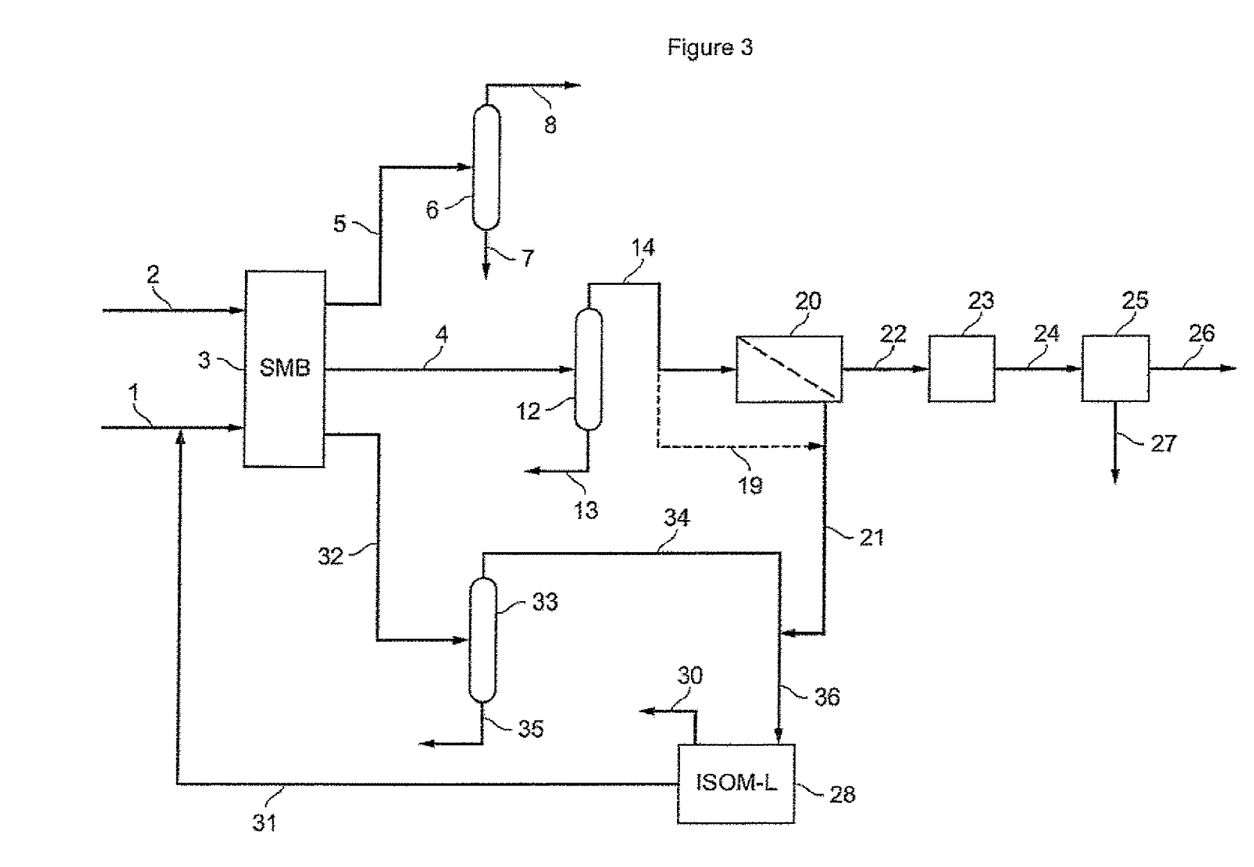
FIG. 3 diagrammatically shows another installation for separation of C8 aromatic compounds for the implementation of the process according to the invention, in which two distilled raffinates R and R* are used.

Reference is now made to FIG. 3, which shows another installation that allows the implementation of the process according to the invention and whose simulated moving bed SMB separation unit produces two separate distilled raffinates R and R*.

The first raffinate that circulates in line 4, which contains the larger part of the ethylbenzene EB, is treated in the same way as for the unit of FIG. 2.

The second raffinate is drawn off downstream from the first raffinate 4 via line 32 and distilled in a column 33 to separate a second distilled raffinate R* that circulates in line 34 from the desorbent that is recycled to the SMB via line 35. This second distilled raffinate R* is relatively low in EB, and relatively high in OX and MX. Consequently, it is not necessary to subject it to a membrane separation to extract from it the ethylbenzene EB that it contains. Thus, according to this preferred variant of the invention, this second distilled raffinate R* is added directly to the retentate that is obtained from the membrane separation unit and that circulates in line 21 to form the feedstock of the isomerization unit 28, preferably in the liquid phase (ISOM-L), supplied via line 36.

The membrane separation unit therefore treats only the first distilled raffinate R and not the total distilled raffinate R+R*. Its capacity and its cost are therefore reduced.

EXAMPLES

The flow rates of the units are expressed in terms of kt/year (1 kt/year 1000 tons per year). The compositions are expressed in terms of % by weight of the stream being considered.

Example 1

According to the Prior Art

This example illustrates the prior art and describes an installation for separation of C8 aromatic compounds according to the installation of FIG. 1:

The total feedstock of the SMB is sent into a simulated moving bed SMB adsorption unit (3) with four zones and four primary streams: the feedstock, the desorbent, the raffinate, and the extract. This unit consists of 24 beds containing a barium-exchanged X zeolite. The temperature is 175° C. The configuration is: 5 beds in zone I, 9 beds in zone II, 7 beds in zone III, and 3 beds in zone IV. The desorbent consists of 99% paradiethylbenzene (PDEB), and the desorbent flow rate is 3000 kt/year.

The flow rate of raffinate (4) is 3780 kt/year. At the bottom of the column (12), 2210 kt/year of desorbent (13) that is recycled to the adsorption unit is drawn off, and at the top of the column, 1570 kt/year of raffinate (14) from which desorbent is removed—whose PX content is about 1%—is drawn off.

The isomerization unit works under the following conditions:

Temperature: 385° C.

Platinum catalyst that contains the EU1 zeolite that is described in the patent FR 2 795 407, page 19 (10% by weight of EU1 zeolite; Si/Al ratio 18; 0.3% by weight of platinum; 89.7% by weight of aluminum that is used as a binder).

Volumetric flow rate: 3.5 h$^{-1}$

H$_2$/hydrocarbon ratio: 4.4:1

Pressure: 0.9 MPa.

It is possible, inside the isomerization unit, to circulate in a loop a stream of 160 kct/year of a C8 and C9 paraffinic and naphthenic fraction (not shown in FIG. 1). This mixture is injected into the isomerization reactor (15). A stream of 130 kt/year of hydrogen is recycled to the isomerization via a compressor.

The primary process streams are as follows:

TABLE 1

|  | Flow Rate (kt/year) | PX (%) | MX (%) | OX (%) | EB (%) |
|---|---|---|---|---|---|
| Fresh Feedstock Line 1 | 460.0 | 25.0 | 45.0 | 20.0 | 10.0 |
| Total SMB Feedstock Lines 1 + 18 | 1980.0 | 21.5 | 47.0 | 21.2 | 10.3 |
| Distilled Extract Line 8 | 410.0 | 99.8 | 0.08 | 0.04 | 0.08 |
| Distilled Raffinate R Line 14 | 1570.0 | 1.0 | 59.2 | 26.7 | 13.0 |
| Isomerizate Recycling Line 18 | 1520.0 | 20.5 | 47.6 | 21.5 | 10.4 |

Example 2

According to the Invention

This example illustrates the invention and describes an installation for separation of C8 aromatic compounds according to the installation of FIG. 2 (except for the treatment part of the ethylbenzene-rich permeate, not presented in detail), therefore with an SMB with a single distilled raffinate R. The flow rate of fresh feedstock (stream 1) is suitable for ensuring a PX production that is approximately identical to that of Example 1.

The simulated moving bed SMB is of the same type and operates in an identical manner to that of FIG. 1.

The distilled raffinate R is sent into a membrane separator that has a mixture selectivity [EB or PX] relative to [MX or OX] of 50, whose zeolite-based selective layer has a mean recovery rate of aromatic compounds in the zeolite of 85%.

A boron-exchanged ZSM-5 membrane is used on a stainless steel substrate, such as the "B-ZSM-55" membrane that is shown in reference (1) (page 568) and in more detail in the references (2) (pages 1202-1203) and (3) (pages 3636-3637), with:

Ref. (1) C. G. Gump, V. A. Tuan, R. D. Noble, J. L. Falconer, Aromatic Permeation through Crystalline Molecular Sieve Membranes, Ind. Eng. Chem. Res., 40 (2001) 565-577

Ref. (2) V. A. Tuan, R. D. Noble, J. L. Falconer, Boron-Substituted ZSM-5 Membranes: Preparation and Separation Performance, AIChE Journal, 46 (2000), 1201-1208

Ref. (3) V. A. Tuan, J. L. Falconer, R. D. Noble, Alkali-Free ZSM-5 Membranes: Preparation Conditions and Separation Performance, Ind. Eng. Chem. Res., 38 (1999) 3635-3646.

This membrane comprises four ZSM-5 membrane layers on a stainless steel substrate with a characteristic pore size of 500 nanometers.

The retentate (line 21) that is low in EB is sent into an isomerization unit in the liquid phase that operates under the following conditions:

Pressure: 2 MPa

Temperature; 260° C.

Catalyst that is described in the U.S. Pat. No. 3,856,871 (column 9, line 19 to column 10, line 3), containing 65% HZSM-5 zeolite and 35% alumina Al$_2$O$_3$ binder.

Volumetric flow rate: 3 h$^{-1}$

The primary process streams are as follows:

TABLE 2

|  | Flow Rate (kt/year) | PX (%) | MX (%) | OX (%) | EB (%) |
|---|---|---|---|---|---|
| Fresh Feedstock Line 1 | 580.0 | 25.0 | 45.0 | 20.0 | 10.0 |
| Total Feedstock Lines 1 + 18 | 1980.0 | 21.0 | 49.9 | 23.7 | 5.3 |
| Distilled Extract Line 8 | 400.0 | 99.8 | 0.08 | 0.04 | 0.08 |
| Distilled Raffinate R Line 14 | 1580.0 | 1.0 | 62.6 | 29.7 | 6.7 |
| Permeate Line 22 | 83.0 | 6.4 | 15.4 | 8.2 | 70.0 |
| Retentate Line 21 | 1400.0 | 0.6 | 65.9 | 30.1 | 3.4 |
| Recycling Line 31 | 1400.0 | 19.3 | 52.0 | 25.3 | 3.4 |

It is possible to note that the recycling of the isomerized product (line 31) is lower than that of the prior art (line 18 of Example 1), with a single isomerization in the liquid phase that is much less expensive in terms of an investment than in terms of operating costs.

Example 3

According to the Invention

This example illustrates the invention and describes an installation for separation of C8 aromatic compounds in accordance with the installation of FIG. 3 (except for the treatment part of the ethylbenzene-rich permeate, not presented in detail), therefore with an SMB with two distilled raffinates R and R*. The flow rate of fresh feedstock (stream 1) is suitable for ensuring a production of PX that is approximately identical to those of Examples 1 and 2.

The SMB adsorption and separation unit is modified this time and produces 3 effluents including two distilled raffinates R and R* whose characteristics will be provided below.

The distribution of the zones is as follows: 5 beds in zone I; 9 beds in zone II; 5 beds in zone IIIA; 3 beds in zone IIIB, and 2 beds in zone IV. It is also possible to refer to the patent FR 2 962 638, page 18, lines 21-22.

The entire first distilled raffinate (or intermediate raffinate) R is sent into a membrane separator that has a membrane of the same type as that of Example 2. The retentate (line 21) that is low in EB is treated with the second distilled raffinate R* (line 34), and the mixture (line 36) is sent into an isomerization unit tin the liquid phase that operates under the same conditions as those of Example 2.

The primary process streams are as follows:

TABLE 3

|  | Flow Rate (kt/year) | PX (%) | MX (%) | OX (%) | EB (%) |
|---|---|---|---|---|---|
| Fresh Feedstock Line 1 | 457 | 25.0 | 45.0 | 20.0 | 10.0 |
| Total Feedstock Lines 1 + 18 | 1980 | 20.6 | 50.8 | 23.7 | 4.9 |
| Distilled Extract Line 8 | 400 | 99.8 | 0.08 | 0.04 | 0.08 |
| 1$^{st}$ Distilled Raffinate R Line 14 | 300 | 2.4 | 54.6 | 27.0 | 16.0 |
| 2$^{nd}$ Distilled Raffinate R* Line 24 | 1280 | 0.1 | 65.1 | 30.9 | 3.8 |
| Permeate Line 22 | 57 | 6.4 | 15.4 | 8.2 | 70.0 |
| Retentate Line 21 | 243 | 1.5 | 63.8 | 31.4 | 3.3 |
| Recycling Line 31 | 1523 | 19.3 | 52.0 | 25.3 | 3.4 |

It is possible to note that the recycling of the isomerized product (line 31) remains very slightly lower than that of the prior art (line 18 of Example 1), with a single isomerization in the liquid phase that is much less costly in terms of an investment than in terms of an operating cost. The flow rate that supplies the membrane separator is greatly reduced relative to that of Example 2 (300 kt/year instead of 1570 kt/year). In contrast, the SMB is a little more complex.

The preceding examples can be repeated with similar success by substituting the generically or specifically described reactants and/or operating conditions of this invention for those used in the preceding examples.

The entire disclosures of all applications, patents and publications, cited herein and of corresponding French application Ser. No. 07/07290, filed Oct. 18, 2007 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing paraxylene from an aromatic hydrocarbon feedstock containing xylenes and ethylbenzene, said process comprising:
   introducing said aromatic hydrocarbon feedstock and a desorbent into an adsorption separation stage having a simulated moving bed, and removing from said adsorption separation stage an extract E, at least one raffinate R comprising ethylbenzene, and another raffinate R* having an ethylbenzene content which is less than that of R;
   distilling said extract E to obtain product paraxylene comprising at least 95% paraxylene and desorbent;
   distilling said at least one raffinate R comprising ethylbenzene to obtain a first distilled raffinate and desorbent;
   distilling said another raffinate R* having an ethylbenzene content which is less than that of R to obtain a second distilled raffinate and desorbent;
   introducing at least part of said first distilled raffinate into a membrane separation stage, wherein said at least part of said distilled raffinate is separated by membrane separation through a zeolitic-type membrane selective for ethylbenzene relative to orthoxylene and to metaxylene, to produce a first fraction F1 enriched in ethylbenzene and at least one additional fraction F2 which is depleted in ethylbenzene;
   combining said at least one additional fraction F2 depleted in ethylbenzene and said second distilled raffinate to form a mixture;
   introducing said mixture of at least one additional fraction F2 depleted in ethylbenzene said second distilled raffinate into a single liquid phase isomerization stage operating at a temperature of between 200° C. and 260° C., a pressure of between 2 MPa and 3 MPa, and an hourly volumetric flow rate encompassed between 2 h$^{-1}$ and 4 h$^{-1}$ to produce an isomerate;
   recycling said isomerate to said aromatic hydrocarbon feedstock at a point upstream of said adsorption separation stage having a simulated moving bed, and
   subjecting at least a portion of said first fraction F1 enriched in ethylbenzene to dehydrogenation.

2. A process according to claim 1, in which all of said effluent from said single liquid phase isomerization stage is recycled to a point upstream of said separation stage, after having optionally been subjected to a separation and evacuation of compounds that do not have 8 carbon atoms.

3. A process according to claim 1, further comprising purifying said first fraction F1 enriched in ethylbenzene to obtain ethylbenzene with a purity of at least equal to 98%.

4. A process according to claim 3, in which the purification of said first fraction F1 enriched in ethylbenzene is conducted by a purification process comprising simple and/or azeotropic distillation and/or liquid-liquid extraction, with or without complexing in the presence of an ionic or non-ionic liquid.

5. A process according to claim 3, wherein the purified first fraction F1 enriched in ethylbenzene is subjected to dehydrogenation for conversion of ethylbenzene into styrene.

6. A process according to claim 3, wherein the purified ethylbenzene-enriched fraction F1 is subjected to dehydrogenation for conversion of ethylbenzene into styrene.

7. A process according to claim 4, wherein the purified first fraction F1 enriched in ethylbenzene is subjected to dehydrogenation for conversion of ethylbenzene into styrene.

8. A process according to claim 1, wherein said zeolitic-type membrane has an ethylbenzene permeability of more than 0.1 barrer.

9. A process according to claim 1, wherein said zeolitic-type membrane has a selectivity toward ethylbenzene relative to orthoxylene and metaxylene of more than 25.

10. A process according to claim 1, wherein the pressure difference between upstream and downstream of the zeolitic-type membrane is between 0.1 and 10 MPa.

11. A process according to claim 1, wherein the pressure difference between upstream and downstream of the zeolitic-type membrane is between 0.1 and 5 MPa.

12. A process according to claim 1, wherein the temperature of said membrane separation stage is between the ambient temperature and 175° C.

13. A process according to claim 1, wherein the temperature of said membrane separation stage is between the ambient temperature and 120° C.

14. A process according to claim 1, wherein said adsorption separation stage operates at a temperature of between 20° C. and 250° C., and at a pressure between the bubble pressure of xylenes at the operating temperature and 2 MPa, and at a volumetric ratio of desorbent to feedstock between 0.5 and 2.5.

15. A process according to claim 14, wherein said adsorption separation stage operates at a temperature of between 90° C. and 210° C., and at a volumetric ratio of desorbent to feedstock between 1.0 and 1.7.

16. A process according to claim 14, wherein said adsorption separation stage operates at a temperature of between 160° C. and 200° C.

* * * * *